United States Patent [19]

Hamamura et al.

[11] Patent Number: 5,245,060
[45] Date of Patent: Sep. 14, 1993

[54] TERPENE DERIVATIVES AND PROCESS FOR PREPARING THE SAME

[75] Inventors: Kimio Hamamura, Chiba; Yoshio Urawa, Ibaraki; Yukio Narabe, Ibaraki; Yoshihiko Hisatake, Ibaraki; Shizumasa Kijima, Chiba, all of Japan

[73] Assignee: Eisai Co. Ltd., Tokyo, Japan

[21] Appl. No.: 849,967

[22] Filed: Mar. 12, 1992

[30] Foreign Application Priority Data

Mar. 12, 1991 [JP] Japan ............................ 3-046536

[51] Int. Cl.$^5$ ............................................ C07C 101/00
[52] U.S. Cl. ................................. 554/103; 554/114; 560/35; 560/125; 560/168
[58] Field of Search ................... 554/103, 114; 560/35, 560/125, 168

[56] References Cited

U.S. PATENT DOCUMENTS 4,460,786 7/1984 Didier .................................. 560/216
4,695,631 9/1987 Otsuka et al. ........................ 564/248

OTHER PUBLICATIONS

Highly Enantioselective Isomerization of Prochiral Allylamines Catalyzed by Chiral Diphosphine Rhodium(I) Complexes, Preparation of Optically Active Enamines; J. Am. Chem. Soc. 1984, 106, 5208-5217.

Primary Examiner—José G. Dees
Assistant Examiner—Samuel Barts
Attorney, Agent, or Firm—Flynn, Thiel, Boutell & Tanis

[57] ABSTRACT

A terpene derivative represented by the general formula (I):

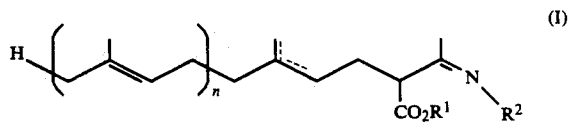

wherein $R^1$ represents a lower alkyl group; $R^2$ represents an alkyl group, a cycloalkyl group, a cycloalkylalkyl group, an aryl group, an arylalkyl group or a heteroaryl group; n is 0 or 1 or 2; and the symbol "........." represents a single or double bond with the proviso that both of the linkages adjacent to each other are not simultaneously single bonds or double bonds which are useful for the preparation of drug, food, perfume and so on, and a process for preparing thereof.

11 Claims, No Drawings

TERPENE DERIVATIVES AND PROCESS FOR PREPARING THE SAME

FIELD OF THE INVENTION

The present invention relates to novel terpenes useful for the preparation of drug, food and perfume, and a process for preparing thereof.

DESCRIPTION OF THE RELATED ART

Various physiological activities represented by in vivo antioxidant activity have been reported with respect to terpenes and have been noted. Such terpenes are not only useful in themselves but also widely used as intermediates for the preparation of drugs food and so on.

Many useful terpenes are known, among which those represented by the following general formula (IV) are used as intermediates or precursors in the preparation of vitamins and perfumes and are therefore required to be prepared in a high yield at a high purity:

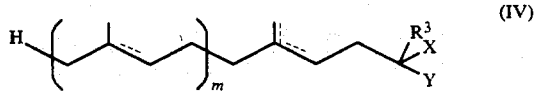

wherein m is 0 or an integer of 1 to 4; $R^3$ represents a hydrogen atom or a group represented by the formula:

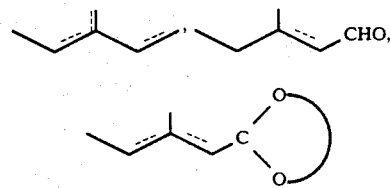

(wherein

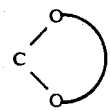

represents a heterocyclic group having two oxygen atoms as heteroatoms),

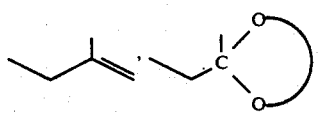

(wherein

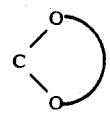

represents a heterocyclic group having two oxygen atoms as heteroatoms), $-OR^4$ (wherein $R^4$ represents a hydrogen atom or an acetyl group, a propionyl group, a benzyl group, a methoxymethyl group or a tetrahydrofurfuryl group),

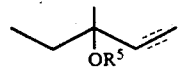

(wherein $R^5$ represents a hydrogen atom or an acetyl group) or

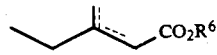

(wherein $R^6$ represents a hydrogen atom, a methyl group or an ethyl group); X and Y are both electron attractive groups or one of them is an electron-attractive group and the other thereof is an electron-donating group; or alternatively, when either of X and Y is an acyl group, the other may form a 5- or 6-membered ring together with $R^3$; in the above definition, the symbol "〰〰" represents a single or double bond and the symbol "═══" represents a double or triple bond. As a process for preparing such terpenes, for example, the following process was proposed in French Patent No. 8414425 (corresponding to Japanese Patent Laid-Open No. 112033/1986) and U.S. Pat. Nos. 4,168,271 and 4,292,459:

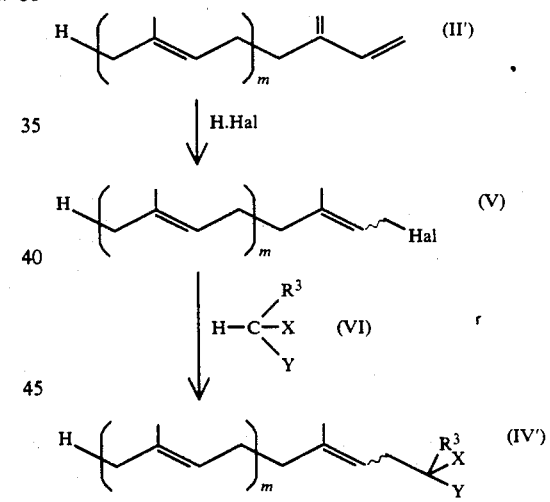

wherein m, X, Y and $R^3$ are each as defined above; and Hal represents a halogen atom.

Specifically, an objective terpene (IV') is prepared by reacting a substituted conjugated diene (II') with a hydrogen halide to form an allyl halide (V) and reacting the halide (V) with a compound (VI) having an active methylene. This process is industrially disadvantageous in that the objective compound is obtained only in a yield as low as 70%, a purity as low as 80% and that cis- and trans-isomers and primary and tertiary allyl halides are formed in the addition reaction of a hydrogen halide to a substituted conjugated diene (II) and the separation and purification of them are very difficult.

Further, another process was proposed in French Patent Nos. 8,015,355 and 8,109,322 (corresponding to Japanese Patent Publication No. 58172/1989). This process is one involving a selective addition of a compound having an activated carbon atom to a substituted conjugated diene, characterized by conducting the reaction in water, or an aliphatic alcohol having 1 to 3 carbon atoms, in the presence of a catalyst system comprising a water-soluble phosphine such as triphenylphosphine sulfonate and metallic rhodium.

According to the above process, however, when the substituted conjugated diene is farnesene, which corresponds to a compound represented by the general formula (II') wherein m is 2, the objective compound (IV') is obtained only at a conversion as low as 43%, though when the diene is myrcene, which corresponds to a compound represented by the general formula (II') wherein m is 1, the objective compound (IV') is obtained at a conversion of 87%. Thus, the process is industrially disadvantageous in respect of yield.

Representative examples of the catalytic component to be used together with metallic rhodium in the above process include water-soluble phosphines represented by the following general formula (VII):

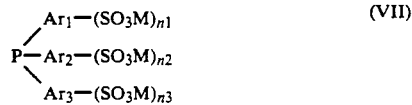

wherein $Ar_1$, $Ar_2$ and $Ar_3$ may be the same or different from each other and each represents a phenylene group or a naphthylene group which may be substituted; M represents an inorganic or organic cationic group; and n1, n2 and n3 may be the same or different from each other and are each an integer of 0 to 3, with the proviso that at least one of them is 1 or above.

SUMMARY OF THE INVENTION

Under these circumstances, the inventors of the present invention have made intensive studies over many years in order to develop a simple process by which the terpene derivative represented by the above general formula (IV) can be prepared in a high yield.

The inventors have made intensive studies in order to improve the yield in preparing the terpene (IV') from farnesene, which corresponds to a compound represented by the general formula (II') wherein m is 2, which is particularly low, as described above, in the above process (described in the Japanese Patent Publication No. 58172/1989), and have found that this object can be attained by the process which will now be described. The present invention has been accomplished on the basis of this finding.

Namely, the present invention relates to a process for preparing a terpene derivative, which comprises reacting an alkyl-substituted conjugated diene represented by the general formula (II):

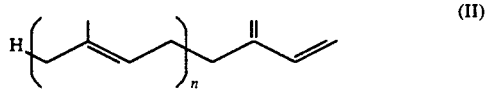

wherein n is 0 or 1 or 2,
with a compound represented by the general formula (III):

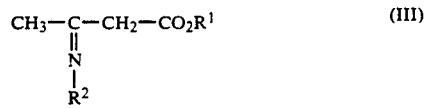

wherein $R^1$ represents a lower alkyl group; and $R^2$ represents an alkyl group, a cycloalkyl group, a cycloalkylalkyl group, an aryl group, an arylalkyl group or a heteroaryl group,
in an organic solvent and in the presence of a transition metal compound and an organic amine to prepare a terpene derivative represented by the general formula (I):

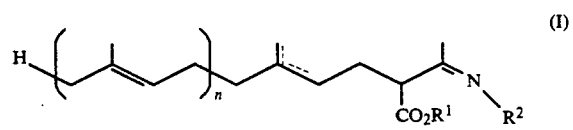

wherein $R^1$ represents a lower alkyl group; $R^2$ represents an alkyl group, a cycloalkyl group, a cycloalkylalkyl group, an aryl group, an arylalkyl group or a heteroalkyl group; n is 0 or 1 or 2; and the symbol "⋯⋯⋯" represents a single or double bond, with the proviso that both of the linkages adjacent to each other must not be simultaneously single bonds or double bonds. The present invention also relates to a terpene derivative represented by the above general formula (I).

The terpene derivative represented by the above general formula (I) is a novel compound and can be used as an intermediate or a precursor for the preparation of vitamins and perfumes, either alone or as a mixture thereof, thus being useful.

DETAILED DESCRIPTION OF THE INVENTION

The lower alkyl group defined with respect to $R^1$ is a straight-chain or branched alkyl group having 1 to 6 carbon atoms and examples thereof include methyl, ethyl, n-propyl, isopropyl, n-butyl, isobutyl, sec-butyl, tert-butyl, pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among these groups, methyl, ethyl, n-propyl and isopropyl groups are desirable and a methyl group is most desirable.

The cycloalkyl group defined with respect to $R^2$ is one having 3 to 8 carbon atoms and examples thereof include cyclopentyl, cyclopropyl, cyclobutyl, cyclohexyl, cycloheptyl and cyclooctyl groups, among which a cyclohexyl group is most desirable.

Preferable examples of the terpene derivative represented by the general formula (I) will now be listed.

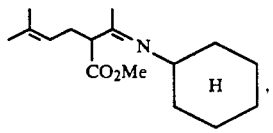

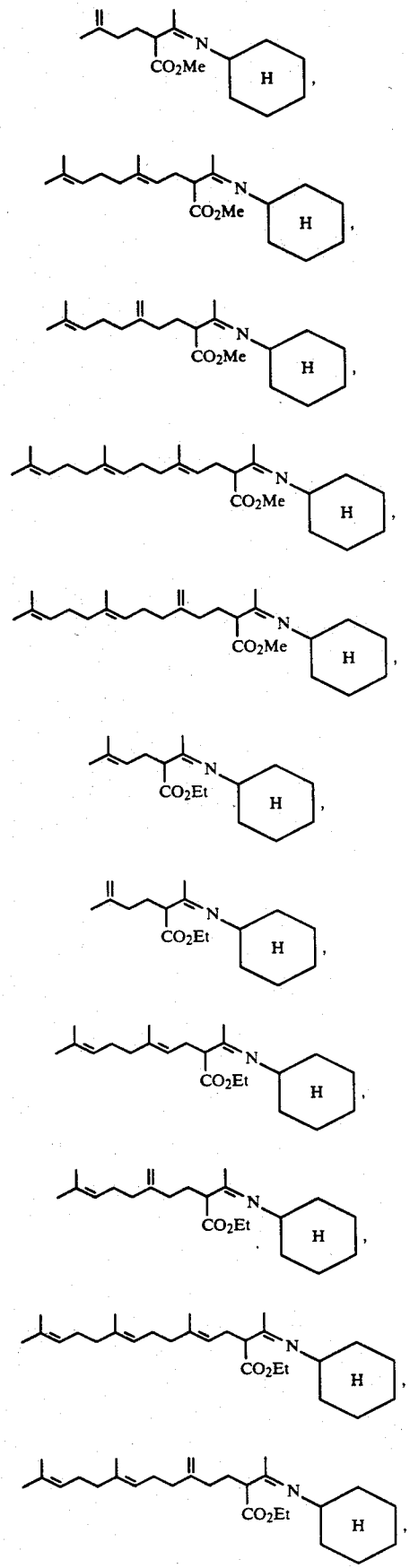
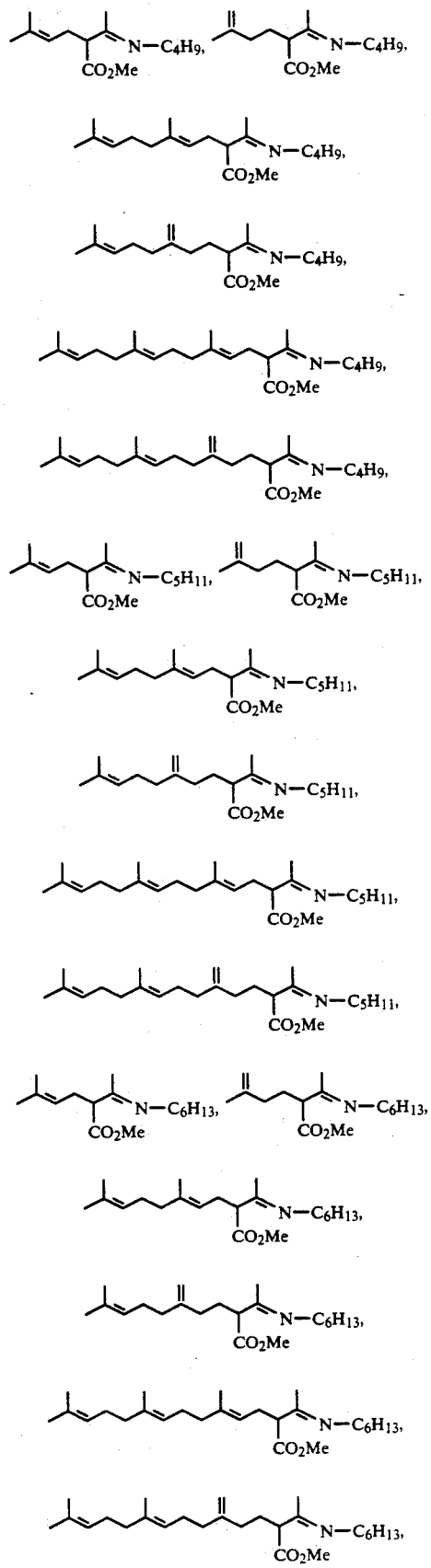

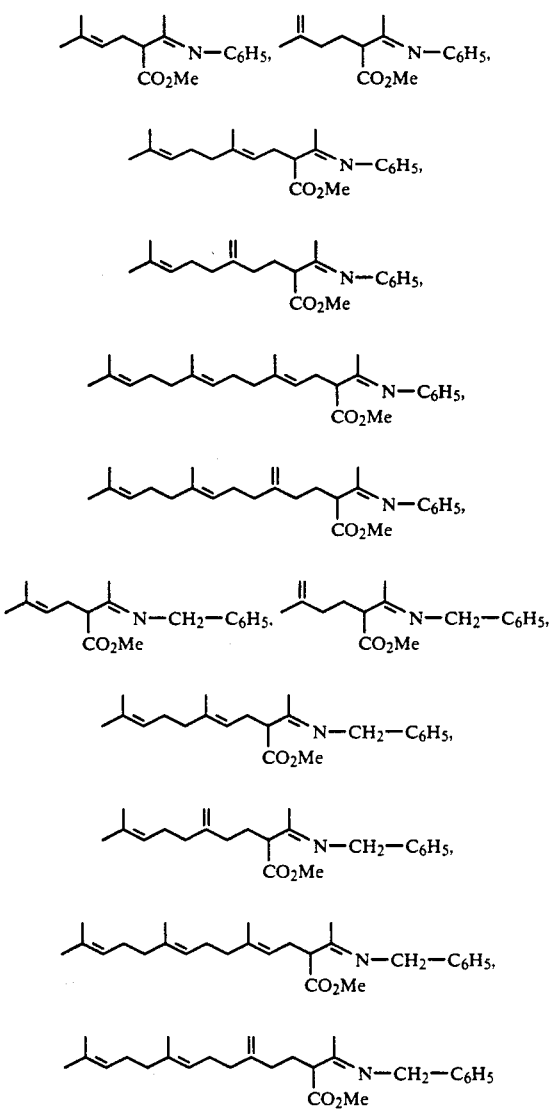

wherein Me represents a methyl group; Et represents an ethyl group; and

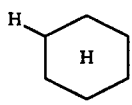

represents a cyclohexyl group.

Most preferable examples of the terpene derivative represented by the general formula (I) is as follows:

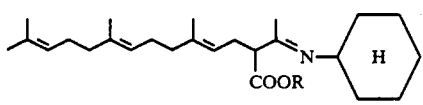

The transition metal compound to be used in the present invention is preferably a rhodium cation complex, for example, [rhodium (cycloocta-1,5-diene)(bisdiphenylphosphinoalkane)] represented by the following general formula (VIII):

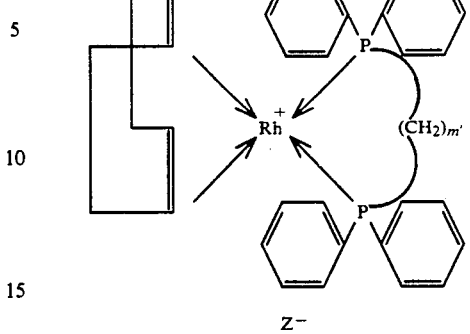

wherein m' is an integer of 2 to 6; and $Z^-$ represents an anion.

Specific examples thereof include [rhodium (cycloocta-1,5-diene)(1,2-bisdiphenylphosphinoethane)] perchlorate, [rhodium (cycloocta-1,5-diene)-(1,3-bisdiphenylphosphinopropane)] perchlorate, [rhodium (cycloocta-1,5-diene)(1,4-bisdiphenylphosphinobutane)] perchlorate, [rhodium (cycloocta-1,5-diene)(1,5-bisdiphenylphosphinopentane)] perchlorate, [rhodium (cycloocta-1,5-diene)(1,6-bisdiphenylphosphinohexane)] perchlorate and [rhodium (cycloocta-1,5-diene)(1,4-bisdiphenylphosphinobutane)] trifluoromethyl sulfite.

The compound represented by the general formula (II) to be used in the present invention includes isoprene, myrcene, β-farnesene and β-springene.

Examples of the compound represented by the general formula (III) to be used in the present invention include methyl 3-cyclohexyliminobutanoate, ethyl 3-cyclohexyliminobutanoate, propyl 3-cyclohexyliminobutanoate, butyl 3-cyclohexyliminobutanoate, pentyl 3-cyclohexyliminobutanoate, methyl 3-butyliminobutanoate, ethyl 3-butyliminobutanoate, propyl 3-butyliminobutanoate, butyl 3-butyliminobutanoate, pentyl 3-butyliminobutanoate, methyl 3-pentyliminobutanoate, ethyl 3-pentyliminobutanoate, propyl 3-pentyliminobutanoate, butyl 3-pentyliminobutanoate, pentyl 3-pentyliminobutanoate, methyl 3-hexyliminobutanoate, ethyl 3-hexyliminobutanoate, propyl 3-hexyliminobutanoate, butyl 3-hexyliminobutanoate, pentyl 3-hexyliminobutanoate, methyl 3-phenyliminobutanoate, ethyl 3-phenyliminobutanoate, propyl 3-phenyliminobutanoate, butyl 3-phenyliminobutanoate, pentyl 3-phenyliminobutanoate, methyl 3-benzyliminobutanoate, ethyl 3-benzyliminobutanoate, propyl 3-benzyliminobutanoate, butyl 3-benzyliminobutanoate and pentyl 3-benzyliminobutanoate.

The organic solvent to be used in the process according to the present invention includes ketones such as acetone and methyl ethyl ketone and esters such as ethyl acetate.

Examples of the organic amine to be used in the present invention include trimethylamine, triethylamine, tripropylamine, tributylamine, tripentylamine, trihexylamine, pyridine, N,N-dimethylaminopyridine, 1,5-diazabicyclo[5.4.0]undecene-5 (DBU) and 1,5-diazabicyclo[4.3.0]nonane-5 (DBN), and the amount thereof is $10^{-4}$ to 1 mol, preferably $10^{-1}$ to 1 mol per mole of the compound represented by the general formula (II).

Now the process for preparing the compound represented by the general formula (I) will be described in more detail.

0.5 g of an organic amine, e.g., trimethylamine, 0.54 g of a conjugated diene represented by the general formula (II), e.g., isoprene, 3.9 g of a compound represented by the general formula (III), e.g., methyl 3-cyclohexyliminobutanoate and 15 ml of acetone are added to 145 mg of a rhodium cation complex represented by the general formula (VIII), e.g., [rhodium (cycloocta-1,5-diene) (1,4-bisdiphenylphosphinobutane)] perchlorate and the obtained mixture is stirred under heating at 100° C. in an autoclave for 6 hours. All of the operations are conducted in an atmosphere of an inert gas such as nitrogen gas or argon gas. The contents of the autoclave are cooled, followed by the addition of 50 ml of n-hexane, by which an orange-yellow crystal is precipitated. This crystal is [rhodium (cycloocta-1,5-diene) (1,4-bisdiphenylphosphinobutane)] perchlorate and can be recovered by filtration and used repeatedly. The filtrate is distilled to remove the solvent and the residue is further distilled in a vacuum to recover 2.3 g of methyl 3-cyclohexyliminobutanoate at 98° to 101° C./0.15 mmHg. Further, the compounds represented by the formulas:

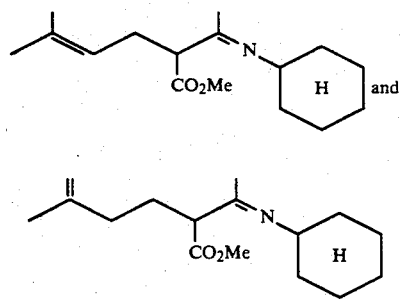

can be obtained, the boiling points of which are each 110° to 115° C./0.15 mmHg.

The above reaction can be conducted at a temperature selected within a range of 60° to 130° C. for a reaction time of 2 to 6 hours. The conversion thereof is 85% or above.

Among the [rhodium (cycloocta-1,5-diene) (bisdiphenylphosphinoalkane)]$^+$ cation complexes represented by the above general formula (VIII) to be used in the present invention, complexes represented by the formula (VIII) wherein m' is 3 to 6 are novel, though those represented by the same formula wherein m' is 2 have been known.

As represented by the following reaction scheme, the rhodium cation complex (VIII) can be prepared by reacting rhodium (cycloocta-1,5-diene) chloride with silver perchlorate in methanol, filtering the reaction mixture to remove formed silver chloride and dropping a solution of bisdiphenylphosphinoalkane in tetrahydrofuran into the filtrate. The obtained rhodium cation complex can be purified by recrystallization from methanol and recovered as an orange-yellow crystal in a yield of 90% or above.

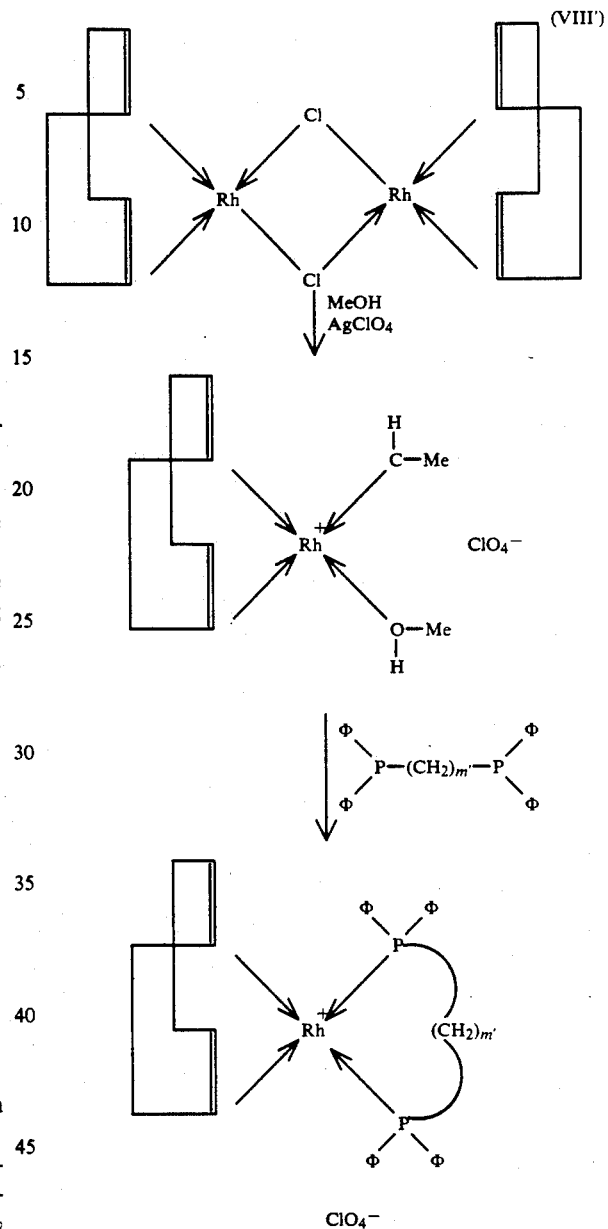

wherein $\phi$ represents a phenyl group.

The rhodium cation complex (VIII) to be used in the present invention is soluble in an organic solvent such as methanol, ethanol, propanol, butanol, methyl acetate, ethyl acetate, acetone, methyl ethyl ketone, pyridine, tetrahydrofuran, dioxane and so on. In practice, the complex can be nearly quantitatively recovered for reuse by conducting the reaction in such an organic solvent and adding n-hexane in which the complex is insoluble to the reaction system.

In the process of the present invention, the amount of the rhodium cation complex to be used is $10^{-4}$ to $10^{-1}$ g atom, preferably $10^{-3}$ to $10^{-2}$ g atom in terms of rhodium atom per mole of the compound represented by the general formula (II).

Since the rhodium cation complex (VIII) according to the present invention has two phosphorus atoms and one rhodium atom in its molecule, it is far superior to the triphenylphosphine metasulfonate (VII) used in the aforementioned French Patent Nos. 8,015,355 and 8,109,322 in respect of coordinating power, so that the active methylene group can add to the 1-position carbon atom of the alkyl-substituted conjugated diene at a high selectivity.

For example, when the substituted conjugated diene (II) is isoprene (n=0), myrcene (n=1) or β-farnesene (n=2), the objective compound (I) can be obtained in a yield of at least 85%, 90% or 91%, respectively, which reveals that the catalytic effect of the rhodium cation complex (VIII) is excellent. The present invention has been accomplished on the basis of this surprising finding.

According to the process of the present invention, the compound (III) can add to the 1-position carbon atom of the substituted conjugated diene (II) at a high selectivity independent of the number (n) of isoprene units of the diene (II), so that the objective terpene derivative (I) can be prepared in a high yield independent of the number (n). Thus, the present invention can be industrially advantageously conducted.

The inventors of the present invention have now found the surprisingly excellent process described above and the advantages of the process are presumed to result from the use of the rhodium cation complex as the transition metal compound.

To mention the above-described prior art (Japanese Patent Publication No. 58172/1989) from such a standpoint, the catalytic activity of the catalyst used therein lowers as the solubility of the substituted conjugated diene used as the raw material in fat or oil becomes higher, which is presumed to be a reason why the yield of the objective terpene according to the prior art lowers as the number (n) of the isoprene units increases.

The excellent effect of the present invention will be described below as compared with that of the prior art.

The compound (I) prepared according to the present invention can be converted into geranyl acetone or farnesyl acetone through decarboxylation and deimination, which can be further converted into tetrahydrogeranyl acetone or phytone through catalytic reduction. These compounds were identified by comparing them with those prepared by other processes.

A scheme from a terpene derivative according to the present invention, which is an intermediate to a final product (dl-α-tocopherol), is as follows:

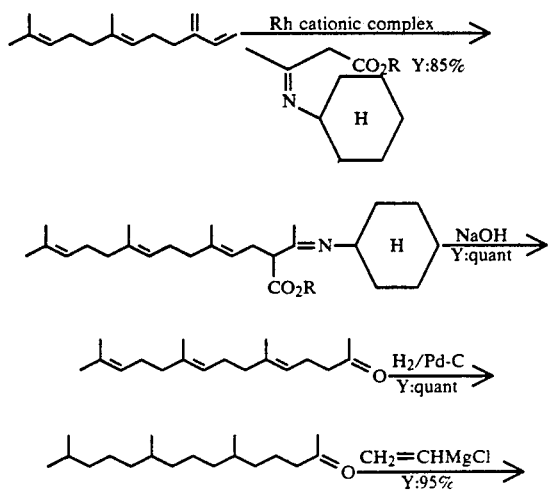

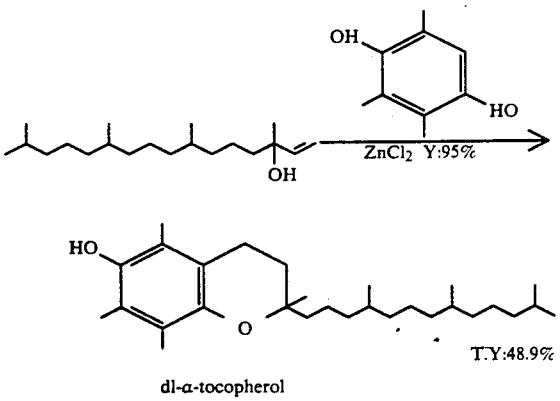

dl-α-tocopherol

The final products derived from the compounds represented by the general formula (I) exhibit various physiological activities represented by in vivo antioxidant activity. Such a final product, for example, free-tocopherol, is not only useful as it is but also widely used in the form of derivatives thereof as drugs, foods and feeds.

Representative examples according to the present invention will now be described, though it is needless to say that the present invention is not limited to them.

EXAMPLES 1 AND 2

Addition of methyl 3-cyclohexyliminobutanoate to isoprene to form compounds represented by the following formulas (a) and (a'):

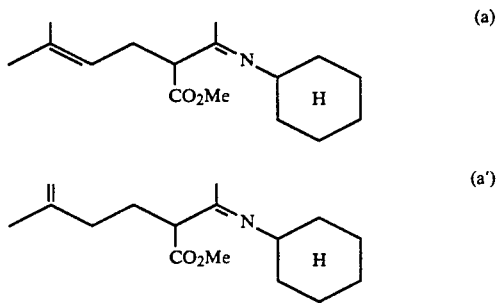

EXAMPLE 1

145 mg of [rhodium (cycloocta-1,5-diene) (1,4-bisdiphenylphosphinobutane)] perchlorate (in the subsequent Examples, abbreviated to "[Rh(COD)(1,4-DPPB)]$^+$ClO$_4^-$) (corresponding to 0.028 mg atom of rhodium), 0.5 g (5 mmol) of triethylamine, 0.54 g (8 mmol) of isoprene, 3.9 g (20 mmol) of methyl 3-cyclohexyliminobutanoate and 15 ml of acetone were stirred together under heating at 100° C. in an autoclave for 6 hours.

The obtained reaction mixture was cooled, followed by the addition of 50 ml of n-hexane, by which an orange-yellow crystal of [Rh(COD)-(1,4-DPPB)]$^+$ClO$_4^-$ was precipitated. The resulting mixture was filtered to recover 141 mg of the rhodium cation complex.

The filtrate was distilled to remove the solvent and the residue was further distilled in a vacuum to recover 2.3 g of methyl 3-cyclohexyliminobutanoate at 98° to 101° C./0.15 mmHg and 1.8 g of a mixture comprising the compounds (a) and (a') at 110° to 115° C./0.15 mmHg (yield: 84.9%).

The capillary gas chromatographic analysis of this mixture revealed that the mixture comprised 58% of the compound (a) and 42% of the compound (a').

IR(cm$^{-1}$): 1,640, 1,600.

NMR (δ): 9.3~9.4 (d, 1H), 5.15 (t), 4.7 (d), 3.7 (s, 3H), 2.3 (m, 1H), 1.8 (s), 1.75 (s), 1.7 (s), 1.4~1.3 (m, 10H).

Mass: 266, 264.

EXAMPLE 2

A reaction was conducted in a similar manner to that of Example 1 except that 157 mg of [Rh(COD)-(1,4-DPPB)]$^+$CF$_3$SO$_3^-$ (corresponding to 0.028 mg atom of rhodium) and 15 ml of methyl ethyl ketone as a solvent were used.

The obtained reaction mixture was treated in a similar manner to that of Example 1. 153 mg of [Rh(COD)(1,4-DPPB)]$^+$CF$_3$SO$_3^-$ and 2.1 g of methyl 3-cyclohexyliminobutanoate were recovered and 1.75 g of a mixture comprising the objective compounds (a) and (a') was obtained (yield: 82.5%).

The capillary gas chromatographic analysis of this mixture revealed that the mixture comprised 56% of the compound (a) and 44% of the compound (a').

EXAMPLES 3 TO 7

Terpene derivatives were prepared in a similar manner to that of Example 1 except that a reagent listed in Table 1 was used instead of the methyl 3-cyclohexyliminobutanoate. The results are given in Table 1.

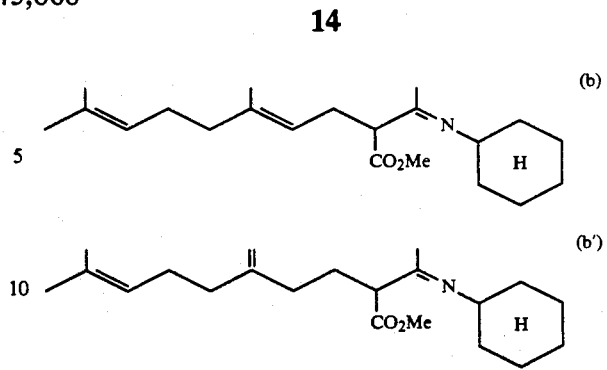

EXAMPLE 8

580 mg (0.8 mmol) of [Rh(COD)(1,4-DPPB)]$^+$ClO$_4^-$ (0.112 mg atom in terms of rhodium), 2.0 g (20 mmol) of triethylamine, 4.4 g (32 mmol) of myrcene, 15.7 g (80 mmol) of methyl 3-cyclohexyliminobutanoate and 45 ml of acetone were stirred together under heating at 100° C. in an autoclave for 6 hours.

The obtained reaction mixture was cooled, followed by the addition of 200 ml of n-hexane, by which an orange-yellow crystal of [Rh(COD)-(1,4-DPPB)]$^+$ClO$_4^-$ was precipitated. The resulting mixture was filtered to recover 564 mg of the rhodium cation complex.

The filtrate was distilled to remove the solvent and the residue was further distilled in a vacuum to recover 9.3 g of methyl 3-cyclohexyliminobutanoate at 96° to 98° C./0.13 mmHg and 9.6 g of a mixture comprising the objective compounds (b) and (b') at 158° to 160° C./0.13 mmHg (yield: 90.0%).

The capillary gas chromatographic analysis of this mixture revealed that the mixture comprised 55% of the compound (b) and 45% of the compound (b').

IR(cm$^{-1}$): 1,640, 1,600.

TABLE 1

| Ex. No. | Iminobutanoate | | Product | Yield |
|---|---|---|---|---|
| 3 | CH$_3$—C(=N—C$_4$H$_9$)—CH$_2$—CO$_2$Me | 3.4 g | [structure with N—C$_4$H$_9$, CO$_2$Me] | 4.19 g 87.8% |
| 4 | CH$_3$—C(=N—C$_5$H$_{11}$)—CH$_2$—CO$_2$Me | 3.7 g | [structure with N—C$_5$H$_{11}$, CO$_2$Me] | 4.51 g 89.1% |
| 5 | CH$_3$—C(=N—C$_6$H$_{13}$)—CH$_2$—CO$_2$Me | 4.0 g | [structure with N—C$_6$H$_{13}$, CO$_2$Me] | 4.75 g 88.8% |
| 6 | CH$_3$—C(=N—C$_6$H$_5$)—CH$_2$—CO$_2$Me | 3.82 g | [structure with N—C$_6$H$_5$, CO$_2$Me] | 4.47 g 86.3% |
| 7 | CH$_3$—C(=N—CH$_2$—C$_6$H$_5$)—CH$_2$—CO$_2$Me | 4.1 g | [structure with N—CH$_2$—C$_6$H$_5$, CO$_2$Me] | 4.77 g 87.2% |

EXAMPLES 8 AND 9

Addition of methyl 3-cyclohexyliminobutanoate to myrcene to form compounds represented by the following formulas (b) and (b'):

NMR (δ): 9.4 (d, 1H), 5.1~5.15 (m), 4.75 (d), 3.65 (s, 3H), 2.35 (m, 1H), 2.0~2.2 (m), 1.7 (s), 1.6 (s), 1.5 (s), 1.2~1.45 (m, 10H).

Mass: 334, 332.

EXAMPLE 9

145 mg (0.2 mmol) of [Rh(COD) (1,4-DPPB)]+ClO4− (0.028 mg atom in terms of rhodium), 0.5 g (5 mmol) of triethylamine, 1.1 g (8 mmol) of myrcene, 3.9 g (20 mmol) of methyl 3-cyclohexyliminobutanoate and 15 ml of methyl ethyl ketone were mixed and stirred together under reflux for 3 hours.

The obtained reaction mixture was cooled, followed by the addition of 50 ml of n-hexane, by which an orange-yellow crystal was precipitated. The resulting mixture was filtered to recover 138 mg of the rhodium cation complex.

The filtrate was treated in a similar manner to that of the Example 8. 2.35 g of a mixture comprising the objective compounds (b) and (b') was obtained (yield: 88.0%).

The capillary chromatographic analysis of this mixture revealed that the mixture comprised 57% of the compound (b) and 43% of the compound (b').

EXAMPLES 10 TO 14

Terpene derivative were prepared in a similar manner to that of the Example 8 except that a reagent listed in Table 2 was used instead of the methyl 3-cyclohexyliminobutanoate. The results are given in Table 2.

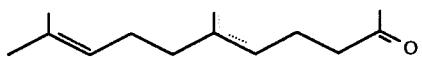

4.6 g (34 mmol) of myrcene, 500 mg (0.68 mmol) of [Rh(COD)(1,4-DPPB)]+ClO4−, 2 g (20 mmol) of triethylamine, 15.7 g (80 mmol) of methyl 3-cyclohexyliminobutanoate and 45 ml of methyl ethyl ketone were treated in a similar manner to that of the Example 8 to form the compounds (b) and (b'):

Geranylacetone can be prepared by the following process.

The reaction mixture prepared above was filtered to recover 478 mg of an orange yellow crystal and the filtrate was concentrated to give an oily residue. 14 g of NaOH, 120 ml of methanol and 60 ml of water were added to the residue and the obtained mixture was stirred under reflux for 3 hours.

The obtained reaction mixture was extracted with 50 ml of n-hexane twice and the n-hexane layers were dried and distilled to remove the solvent. The obtained residue was further distilled in a vacuum to give 5.32 g of the objective compound having a boiling point of 70° to 74° C. (0.5 mmHg) (yield: 80.5%).

Part of the geranylacetone prepared above was catalytically reduced into tetrahydrogeranylacetone, which was identified by IR, NMR and capillary gas chromatography by the use of the same compound prepared by other processes as the reference.

TABLE 2

| Ex. No. | Iminobutanoate | | Product | Yield | |
|---|---|---|---|---|---|
| 10 | CH3—C(=N—C4H9)—CH2—CO2Me | 3.42 g | [structure with N—C4H9, CO2Me] | 5.63 g | 91.5% |
| 11 | CH3—C(=N—C5H11)—CH2—CO2Me | 3.7 g | [structure with N—C5H11, CO2Me] | 5.96 g | 92.7% |
| 12 | CH3—C(=N—C6H13)—CH2—CO2Me | 4.0 g | [structure with N—C6H13, CO2Me] | 6.1 g | 90.9% |
| 13 | CH3—C(=N—C6H5)—CH2—CO2Me | 3.82 g | [structure with N—C6H5, CO2Me] | 5.92 g | 90.2% |
| 14 | CH3—C(=N—CH2—C6H5)—CH2—CO2Me | 4.1 g | [structure with N—CH2—C6H5, CO2Me] | 6.13 g | 89.5% |

EXAMPLE 15

Synthesis of Geranylacetone

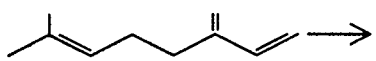

EXAMPLES 16 TO 20

Geranylacetone was prepared in a similar manner to that of the Example 15 except that the solvent, catalyst and organic amine used were those listed in Table 3. The results of the capillary gas chromatography of the products are given in Table 3.

TABLE 3

| Ex. No. | Myrcene | Catalyst | Organic amine | Solvent | Reaction condn. | Results of capillary gas chromatography |
|---|---|---|---|---|---|---|
| 16 | 4.6 g (34 mmol) | [Rh(COD) (1,4-DPPB)]+ ClO4− 0.5 g | pyridine 3 g | toluene | 120° C. 6 hr | 76.1% |
| 17 | 4.6 g (34 mmol) | [Rh(COD) (1,4-DPPB)]+ ClO4− 0.5 g | tributylamine 3 g | methyl ethyl ketone | 90° C. 3 hr | 89.3% |
| 18 | 4.6 g (34 mmol) | [Rh(COD) (1,3-DPPP)]+ ClO4− 0.52 g | triethylamine 2 g | methyl ethyl ketone | 90° C. 3 hr | 58.5% |
| 19 | 4.6 g (34 mmol) | [Rh(COD) (1,5-DPPP)]+ ClO4− 0.55 g | triethylamine 2 g | methyl ethyl ketone | 90° C. 3 hr | 67.7% |
| 20 | 4.6 g (34 mmol) | [Rh(COD) (1,6-DPPh)]+ ClO4− 0.6 g | triethylamine 2 g | methyl ethyl ketone | 90° C. 3 hr | 33.3% | note)
1,3-DPPP: 1,3-bisdiphenylphosphinopropane
1,5-DPPP: 1,5-bisdiphenylphosphinopentane
1,6-DPPh: 1,6-bisdiphenylphosphinohexane

EXAMPLES 21 AND 22

Addition of methyl 3-chlorohexyliminobutanoate to β-farnesene to form compounds represented by the following formulas (c) and (c′):

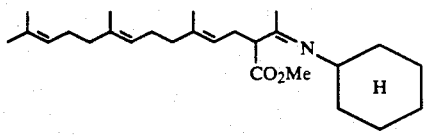
(c)

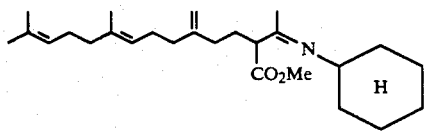
(c′)

EXAMPLE 21

500 mg (0.68 mmol) of [Rh(COD)(1,4-DPPB)]+ClO4−, 2.0 g (20 mmol) of triethylamine, 6.94 g (34 mmol) of β-farnesene, 10.0 g (51 mmol) of methyl 3-cyclohexyliminobutanoate and 45 ml of isopropenyl acetate were mixed and stirred together under reflux for 6 hours.

The reaction mixture was cooled, followed by the addition of 200 ml of n-hexane, by which an orange-yellow crystal was precipitated. The resulting mixture was filtered to recover 483 mg of the rhodium cation complex.

The filtrate was distilled to remove the solvent and the residue was further distilled in a vacuum to recover 3.2 g of methyl 3-cyclohexyliminobutanoate at 100° to 104° C./0.2 mmHg and 12.2 g of a mixture comprising the objective compounds (c) and (c′) at 202° to 205° C./0.13 mmHg (yield: 89.4%).

The capillary gas chromatographic analysis of this mixture revealed that the mixture comprised 57% of the compound (c) and 43% of the compound (c′).
IR(cm−1): 1,640, 1,600.

NMR (δ): 9.4 (d, 1H), 5.0~5.2 (m, olefinic proton), 4.75 (d, exomethylene), 3.65 (s, 3H), 2.3 (m, 1H), 1.9~2.1 (m), 1.8 (s), 1.7 (s), 1.6 (s), 1.2~1.4 (m, 10H).
Mass: 402, 400.

EXAMPLE 22

0.5 g (0.64 mmol) of [Rh(COD)(1,4-DPPB)]+CF3SO3−, 2 g (20 mmol) of triethylamine, 6.94 g (34 mmol) of β-farnesene, 10 g (51 mmol) of methyl 3-cyclohexyliminobutanoate and 45 ml of methyl ethyl ketone were treated in a similar manner to that of the Example 21. 479 mg of (Rh(COD)(1,4-DPPB)]+CF3SO3− and 3.0 g of methyl 3-cylohexyliminobutanoate were recovered and 12.5 g of a mixture, having a boiling point of 196° to 200° C./0.1 mmHg and comprising the objective compounds (c) and (c′), was obtained (yield: 91.6%).

The capillary gas chromatographic analysis of this mixture revealed that the mixture comprised 56.5% of the compound (c) and 43.5% of the compound (c′).

EXAMPLES 23 TO 27

Terpene derivatives were prepared in a similar manner to that of Example 21 except that a reagent listed in Table 4 was used instead of the methyl 3-cyclohexyliminobutanoate. The results are given in Table 4.

TABLE 4

| Ex. No. | Iminobutanoate | | Product | Yield |
|---|---|---|---|---|
| 23 | CH3—C(=N—C4H9)—CH2—CO2Me | 3.42 g | [structure with N—C4H9, CO2Me] | 6.75 g 89.9% |
| 24 | CH3—C(=N—C5H11)—CH2—CO2Me | 3.7 g | [structure with N—C5H11, CO2Me] | 7.14 g 91.7% |

TABLE 4-continued

| Ex. No. | Iminobutanoate | | Product | Yield | |
|---|---|---|---|---|---|
| 25 | CH$_3$—C(=N-C$_6$H$_{13}$)—CH$_2$—CO$_2$Me | 4.0 g | [structure]=N—C$_6$H$_{13}$, CO$_2$Me | 7.29 g | 90.3% |
| 26 | CH$_3$—C(=N-C$_6$H$_5$)—CH$_2$—CO$_2$Me | 3.82 g | [structure]=N—C$_6$H$_5$, CO$_2$Me | 7.16 g | 91.4% |
| 27 | CH$_3$—C(=N-CH$_2$-C$_6$H$_5$)—CH$_2$—CO$_2$Me | 4.1 g | [structure]=N—CH$_2$—C$_6$H$_5$, CO$_2$Me | 7.3 g | 90.1% |

EXAMPLE 28

Synthesis of Farnesylacetone

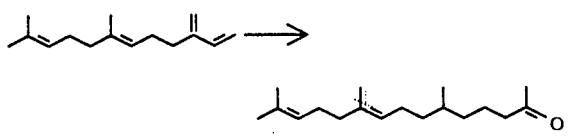

626 mg (0.85 mmol) of [Rh(COD) (1,4-DPPB)]$^+$ClO$_4^-$, 2 g (20 mmol) of triethylamine, 7.0 g (34.3 mmol) of β-farnesene, 10.2 g (52 mmol) of methyl 3-cyclohexyliminobutanoate and 21 ml of acetone were treated in a similar manner to that of Example 21. The compounds (c) and (c') were obtained.

Farnesylacetone can be prepared by the following process.

The reaction mixture obtained above was filtered to recover 608 mg of an orange-yellow crystal and the filtrate was concentrated to give an oily residue. 14 g of NaOH, 150 ml of ethanol and 60 ml of water were added to the residue and the obtained mixture was stirred under reflux for 3 hours.

The reaction mixture was cooled and extracted with 50 ml of n-hexane twice and the n-hexane layers were dried and distilled to remove the solvent. The obtained residue was further distilled in a vacuum to give 8.1 g of the objective compound, the boiling point of which was 120° to 123° C./0.15 mmHg (yield: 90.2%).

Part of the farnesylacetone prepared above was catalytically reduced into phytone, which was identified by IR, NMR and the capillary gas chromatography by the use of the same compound prepared by other processes as the reference.

EXAMPLES 29 TO 40

Farnesylacetone (FA) was prepared in a similar manner to that of the Example 28 except that the solvent, catalyst and organic amine used were those listed in Table 5. Part of the obtained farnesylacetone was catalytically reduced into phytone. The results of the capillary gas chromatography of the products are given in Table 5.

TABLE 5

| | | | | | Results of capillary gas chromatography | |
|---|---|---|---|---|---|---|
| Ex. No. | Catalyst | Organic amine | Solvent | Reaction condn. | content of FA | content of phytone |
| 29 | [Rh(COD) (1,4-DPPB)]$^+$ ClO$_4^-$ 0.6 g | triethylamine 2 g | methyl ethyl ketone | 90° C. 3 hr | 90.9% | 90.1% |
| 30 | [Rh(COD) (1,2-DPPE)]$^+$ ClO$_4^-$ 0.55 g | triethylamine 2 g | methyl ethyl ketone | 90° C. 3 hr | 4.6% | 4.5% |
| 31 | [Rh(COD) (1,3-DPPP)]$^+$ ClO$_4^-$ 0.58 g | triethylamine 2 g | methyl ethyl ketone | 90° C. 3 hr | 16.1% | 15.8% |
| 32 | [Rh(COD) (1,5-DPPP)]$^+$ ClO$_4^-$ 0.62 g | triethylamine 2 g | methyl ethyl ketone | 90° C. 3 hr | 52.2% | 51.4% |
| 33 | [Rh(COD) (1,6-DPPh)]$^+$ ClO$_4^-$ 0.63 g | triethylamine 2 g | methyl ethyl ketone | 90° C. 3 hr | 16.8% | 15.7% |
| 34 | [Rh(COD) (1,4-DPPB)]$^+$ ClO$_4^-$ 0.6 g | tributylamine 2.5 g | tetrahydrofuran | 90° C. 3 hr | 59.2% | 58.5% |
| 35 | [Rh(COD) (1,4-DPPB)]$^+$ ClO$_4^-$ 0.6 g | tributylamine 2.5 g | dioxane | 100° C. 6 hr | 47.9% | 46.9% |
| 36 | [Rh(COD) (1,4-DPPB)]$^+$ ClO$_4^-$ 0.6 g | triethylamine 2 g | ethanol | 110° C. 6 hr | 37.0% | 36.6% |
| 37 | [Rh(COD) (1,4-DPPB)]$^+$ ClO$_4^-$ 0.6 g | triethylamine 2 g | isopropyl ether | 100° C. 6 hr | 19.9% | 19.1% |
| 38 | [Rh(COD) (1,4-DPPB)]$^+$ ClO$_4^-$ 0.6 g | triethylamine 2 g | toluene | 120° C. 6 hr | 12.7% | 12.2% |
| 39 | [Rh(COD) (1,4-DPPB)]$^+$ CF$_3$SO$_3^-$ 0.7 g | triethylamine 2 g | acetone | 90° C. 6 hr | 81.7% | 80.3% |
| 40 | [Rh(COD) (1,4-DPPB)]$^+$ | triethylamine | methyl | 100° C. | 91.5% | 90.7% |

TABLE 5-continued

| Ex. No. | Catalyst | Organic amine | Solvent | Reaction condn. | Results of capillary gas chromatography content of FA | content of phytone |
|---|---|---|---|---|---|---|
| | CF$_3$SO$_3$⁻ 0.7 g | 2 g | ethyl ketone | 3 hr | | | note)
1,2-DPPE: 1,2-bisdiphenylphosphinoethane In Examples 34 to 40, the reaction was conducted in a sealed tube.

COMPARATIVE EXPERIMENT

According to the Example 21 of Rhone-Poulenc patent (Japanese Patent Publication No. 58172/1989), 64 mg of [Rh(COD)Cl]$_2$ (0.26 mg atom in terms of rhodium), 0.53 g of Na-TPPTs (0.78 mg atom in terms of P$^{3+}$), 0.20 g (1.9 mmol) of Na$_2$CO$_3$ and 15 ml of water were put in an autoclave purged with argon.

Then, 3.26 g (16 mmol) of β-farnesene and 11.6 g (58.9 mmol) of methyl 3-cyclohexyliminobutanoate were added to the autoclave. The contents were stirred under heating at 120° C. for 6 hours. The presence of neither the compound (c) nor the compound (c') was observed in the capillary gas chromatographic analysis of the reaction mixture.

What we claim:

1. A terpene derivative represented by the general formula (I):

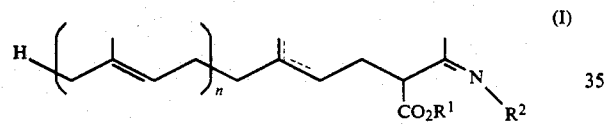

(I)

wherein R$^1$ represents a lower alkyl group; R$^2$ represents an alkyl group, a cycloalkyl group, a cycloalkylalkyl group, an aryl group or an arylalkyl group; n is 0 or 1 or 2; and the symbol "⋯⋯⋯" represents a single or double bond with the proviso that both of the linkages adjacent to each other are not simultaneously single bonds or double bonds.

2. The terpene derivative as set forth in claim 1, wherein said terpene derivative is a compound selected from among those represented by the following chemical formulas:

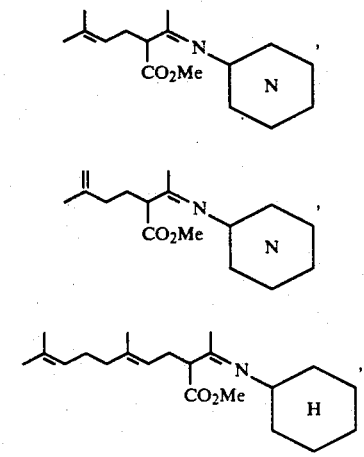

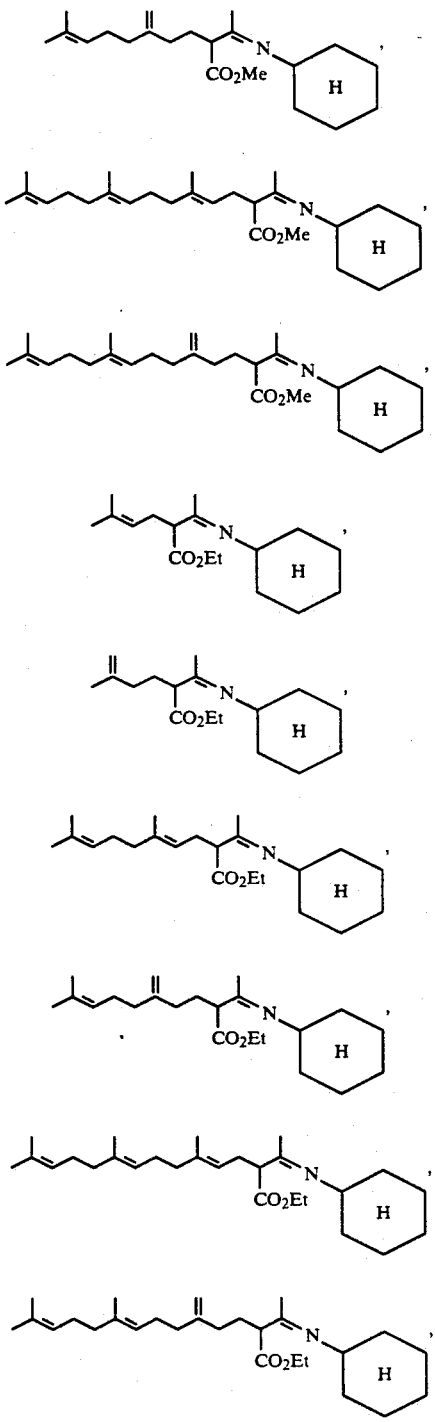

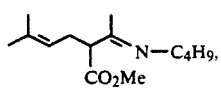

wherein Me represents a methyl group; Et represents an ethyl group; and

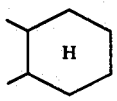

represents a cyclohexyl group.

3. A process for preparing a terpene derivative, which comprises reacting a compound represented by the general formula (II):

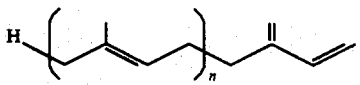

wherein n is 0 or 1 or 2,
with a compound represented by the general formula (III):

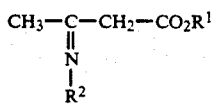

wherein $R^1$ represents a lower alkyl group; and $R^2$ represents an alkyl group, a cycloalkyl group, a cycloalkylalkyl group, an aryl group or an arylalkyl group, in an organic solvent in the presence of a transition metal compound and an organic amine to prepare a terpene derivative represented by the general formula (I):

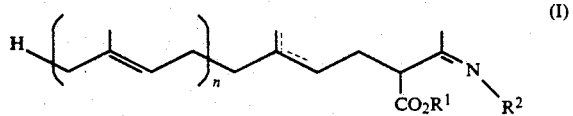

wherein $R^1$ represents a lower alkyl group; $R^2$ represents an alkyl group, a cycloalkyl group, a cylcoalkylalkyl group, an aryl group or an arylalkyl group; n is 0 or 1 or 2; and the symbol " " represents a single or double bond with the proviso that both of the linkages adjacent to each other are not simultaneously single bonds or double bonds.

4. The process as set forth in claim 3, wherein said transition metal compound is a rhodium compound.

5. The process as set forth in claim 3, wherein said transition metal compound is one or more rhodium compound(s) selected from the group consisting of [rhodium (cycloocta-1,5-diene) (1,2-bisdiphenylphosphinoethane)] perchlorate, [rhodium (cycloocta-1,5-diene) (1,3-bisdiphenylphosphinopropane)] perchlorate, [rhodium (cycloocta-1,5-diene) (1,4-bisdiphenylphosphinobutane)] perchlorate, [rhodium (cycloocta-1,5-diene) (1,5-bisdiphenylphosphinopentane)] perchlorate, [rhodium (cycloocta-1,5-diene) (1,6-bisdiphenylphosphinohexane)] perchlorate and [rhodium (cycloocta-1,5-diene) (1,4-bisdiphenylphosphinobutane)] trifluoromethyl sulfite.

6. The process as set forth in claim 4, wherein the rhodium compound is used in an amount of $10^{-4}$ to $10^{-1}$ g atom in terms of rhodium metal per mole of the compound represented by the general formula (II).

7. The process as set forth in claim 3, wherein the compound represented by the general formula (II) is one selected from the group consisting of isoprene, myrcene, β-farnesene and β-springene.

8. The process as set forth in claim 3, wherein the compound represented by the general formula (III) is one selected from the group consisting of methyl 3-cyclohexyliminobutanoate, ethyl 3-cyclohexyliminobutanoate, propyl 3-cyclohexyliminobutanoate, butyl 3-cyclohexyliminobutanoate, pentyl 3-cyclohexyliminobutanoate, methyl 3-butyliminobutanoate, ethyl 3-butyliminobutanoate, propyl 3-butyliminobutanoate, butyl 3-butyliminobutanoate, pentyl 3-butyliminobutanoate, methyl 3-pentyliminobutanoate, ethyl 3-pentyliminobutanoate, propyl 3-pentyliminobutanoate, butyl 3-pentyliminobutanoate, pentyl 3-pentyliminobutanoate, methyl 3-hexyliminobutanoate, ethyl 3-hexyliminobutanoate, propyl 3-hexyliminobutanoate, butyl 3-hexyliminobutanoate, pentyl 3-hexyliminobutanoate, methyl 3-phenyliminobutanoate, ethyl 3-phenyliminobutanoate, propyl 3-phenyliminobutanoate, butyl 3-phenyliminobutanoate, pentyl 3-phenyliminobutanoate, methyl 3-benzyliminobutanoate, ethyl 3-benzyliminobutanoate, propyl 3-benzyliminobutanoate, butyl 3-benzyliminobutanoate and pentyl 3-benzyliminobutanoate.

9. The process as set forth in claim 3, wherein said organic amine is selected from the group consisting of trimethylamine, triethylamine, tripropylamine, tributylamine, tripentylamine, trihexylamine, pyridine, N,N-dimethylaminopyridine, 1,5-diazabicyclo[5.4.0]undecene-5 (DBU) and 1,5-diazabicyclo[4.3.0]nonane-5 (DBN), and the amount thereof is $10^{-4}$ to 1 mol per mole of the compound represented by the general formula (II).

10. A terpene derivative represented by the general formula (X):

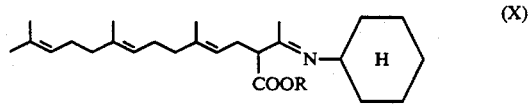

wherein R represents a methyl group or an ethyl group.

11. A process for preparing a terpene derivative, which comprises reacting a compound represented by the general formula (Y):

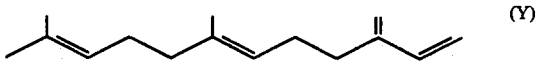

with a compound represented by the general formula (Z):

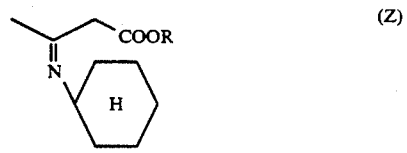

wherein R represents a methyl group or an ethyl group, in an organic solvent in the presence of rhodium (cycloocta-1,5-diene) (1,4-bisdiphenylphosphinobutane)

perchlorate and an organic amine to prepare a terpene derivative represented by the general formula (X):
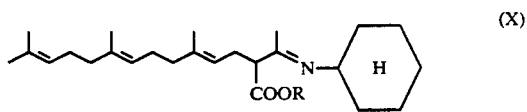
wherein R represents a methyl group or an ethyl group.
* * * * *

UNITED STATES PATENT AND TRADEMARK OFFICE
CERTIFICATE OF CORRECTION

PATENT NO.   :   5 245 060
DATED        :   September 14, 1993
INVENTOR(S)  :   Kimio HAMAMURA et al It is certified that error appears in the above-identified patent and that said Letters Patent is hereby corrected as shown below:

Column 21, lines 50-60; change

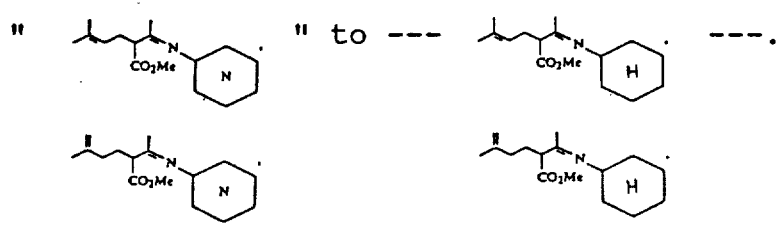

Column 25, line 46; change "  " to ---"......"---.

Signed and Sealed this

Twenty-sixth Day of April, 1994

Attest:

BRUCE LEHMAN

Attesting Officer        Commissioner of Patents and Trademarks